United States Patent [19]

Sandhu et al.

[11] Patent Number: 5,731,150
[45] Date of Patent: Mar. 24, 1998

[54] IS6110 BASED MOLECULAR DETECTION OF MYCOBACTERIUM TUBERCULOSIS

[75] Inventors: Gurpreet S. Sandhu; Bruce C. Kline; Leslie Stockman; Glenn D. Roberts, all of Rochester, Minn.; Marcia E. Lewis, Cohasset, Mass.

[73] Assignee: Chiron Diagnostic Corporation, East Walpole, Mass.

[21] Appl. No.: 551,645

[22] Filed: Nov. 1, 1995

[51] Int. Cl.$^6$ .............................. C12Q 1/68; C12P 19/34; C07H 21/04; C07H 21/00
[52] U.S. Cl. .................... 435/6; 435/91.2; 536/22.1; 536/24.3; 536/25.32
[58] Field of Search ............... 435/91.2, 6; 536/22.1, 536/24.3, 25.38

[56] References Cited

U.S. PATENT DOCUMENTS

| | | | |
|---|---|---|---|
| 4,851,330 | 7/1989 | Kohne | 435/6 |
| 4,965,188 | 10/1990 | Mullis et al. | 435/91 |
| 5,168,039 | 12/1992 | Crawford et al. | 435/6 |
| 5,370,998 | 12/1994 | Crawford et al. | 435/91.2 |

FOREIGN PATENT DOCUMENTS

| | | | |
|---|---|---|---|
| 0461045 | 6/1991 | European Pat. Off. . | |
| 0552571 A1 | 12/1992 | European Pat. Off. | C12N 1/06 |
| 0556521 | 12/1992 | European Pat. Off. . | |
| 0628640 A1 | 12/1992 | European Pat. Off. | C12Q 1/68 |
| 9002821 | 3/1990 | WIPO . | |
| WO 94/17203 | 8/1994 | WIPO | C12Q 1/68 |

OTHER PUBLICATIONS

Delacourt, C., et al. "Use of polymerase chain reaction for improved diagnosis of tuberculosis in children", *The Journal of Pediatrics*, vol. 126, No. 5, pp. 703–709 (1995).

Thierry et al. IS6110, an IS-like element of Mycobacteria Tuberculosis Complex, Nucleic Acids Research, 1990, vol. 18, No. 1,188.

Sambrook et al. Molecular Cloning A Laboratory Manual, 1982 pp. 89–91.
Abe et al. J. Clin. Microbiol., 31:3270–3274, 1993.
Brisson–Noel et al. Lancet 338:364–366, 1991.
Calos and Miller, Cell 20:579–595, 1980.
Cave et al. Molecular and Cellular Probes, 5:73–80, 1991.
Chomczynski and Sacchi, Analytical Biochemistry 162:156–159, 1987.
Chou et al. Nucleic Acids Res. 20:1717–1723, 1992.
Clarridge et al. Journal of Clinical Microbiology 31:2049–2056, 1993.
Cormican et al. J. Clin. Pathology 45:601–604, 1992.
Cousins et al. J. Clinical Microbiol. 30: 255–258, 1992.

(List continued on next page.)

*Escherichia coli* transposon Tn3411, Accession M19532.
*Agrobacterium tumefaciens* Ti plasmid, Accession x55075.

*Primary Examiner*—Stephanie W. Zitomer
*Assistant Examiner*—Joyce Tung
*Attorney, Agent, or Firm*—Arthur S. Morgenstern; Robert P. Blackburn; Mark A. Kassel

[57] ABSTRACT

The detection of the IS6110 insertion element in a clinical specimen is a rapid way of diagnosing infection by *Mycobacterium tuberculosis*. A reliable diagnostic test for tuberculosis based on the IS6110 DNA is described in this disclosure. A "Universal" specimen preparation protocol that eliminates live organisms and purifies nucleic acids from all types of clinical specimens is described. Two nucleic acid primers designed to amplify IS6110 DNA with high specificity in a polymerase chain reaction are also described. The amplified IS6110 DNA is identified by a restriction endonuclease and electrophoresis based assay. The identification process also renders the DNA unamplifiable in a subsequent PCR, thereby reducing the possibility of contaminating other specimens. Time, labor and cost is minimized, while user safety and test reliability are maximized. The complete DNA extraction, amplification and analysis is accomplished with ease within an 8 hour period, with a sensitivity of 92% and a specificity approaching 100%. Testing of serially obtained samples from the same patient increases the overall rate of detection to 100%.

19 Claims, 4 Drawing Sheets

OTHER PUBLICATIONS

Del Portillo et al, J. Clinical Microbiol. 29:2163–2168, 1991.
Dolin et al, Bulletin of the W.H.O., 72:213–220, 1994.
Eisenach et al, J. Infectious Diseases 161:977–981, 1990.
Fidler et al, Tubercle and Lung disease, 74: 414–415, 1993.
Folgueira et al, Neurology 44:1336–1338, 1994.
Forbes and Hicks. J. Clin Microbiol. 31:1688–1694, 1993.
Forbes, Clin. Microbiol. Newsletter, 17:145–150, 1995.
Hermans et al, J. Clin. Microbiol. 28:1204–1213, 1990.
Kaltwasser et al, Molecular & Cellular Probes 7:465–470, 1993.
Kent et al, J. Clin. Microbiol. 33:2290–2293, 1995.
Kocagoz et al, J. Clin. Microbiol. 31:1435–1438, 1993.
Kolk et al, J. Clin. Microbiol. 30:2567–2575, 1992.
Kox et al, J. Clin. Microbiol. 32:672–678, 1994.
Lee et al, J. Neurological Sciences 123:173–179, 1994.
Liu et al, Neurology 44:1161–1164, 1994.
Mariani et al, Journal of General Microbiology 139:1767–1772, 1993.
Miller et al, J. Clin. Microbiol. 32:393–397, 1994.
Noordhoek et al, J. Clin. Microbiol. 32:277–284, 1994.
Pao et al, J. Clin. Microbiol. 28:1877–1880, 1990.
Reischl et al, Biotechniques 17: 844–845, 1994.
Saiki et al, Science, 239:487–491, 1988.
Schluger et al, Chest 105:1116–1121, 1994.
Shawar et al, J. Clin. Microbiol. 31:61–65, 1993.
Sommer et al, Mayo Clinic proceedings, 64:1361–1372, 1989.
Spargo et al, Molecular and Cellular probes, 7:395–404, 1993.
Thierry et al, J. Clin. Microbiol., 28:2668–2673, 1990.
Thierry et al, Nucleic Acids Research, 18:188, 1990.
Wilson et al, J. Clin. Microbiol. 31:776–782, 1993.
Zambardi et al, Annales de Biologie Clinique 50:893–897, 1993.
Zwadyk Jr. et al, J. Clin. Microbiol. 32:2140–2146, 1994.
*Mycobacterium tuberculosis* insertion sequence IS6110, Accession X17348, M29899.
*Mycobacterium smegmatis* insertion sequence IS1137, Acession x70913.
*Pseudomonas syringae* insertion sequence IS51, Accession M14365.
*Pseudomonas cepacia* insertion sequence IS401, Accession L09108.

FIGURE 3

```
                                          Crawford        SEQ ID: 1
5'     ggaccacgatcgctgatccggccacagcccgtcccgccgat ctcgtccagcgccgcTTCG
    721 ---------+---------+---------+---------+- --------+---------+ 780
3'     cctggtgctagcgactaggccggtgtcgggcagggcggcta gagcaggtcgcggcgaagc SalI
       GACCACCAGCACCTAACC ggctgtgggtagcagacctcacctatgtgtcgacctgggcag
    781 ---------+-------- -+---------+---------+---------+---------+ 840
       ctggtggtcgtggattgg ccgacacccatcgtctggagtggatacacagctggacccgtc BamHI
       ggttcgcctacgtggcctttgtca ccgacgcctacgCtcgcagg atcctgggctggcgggt
    841 ---------+---------+---- -----+---------+----- -----+---------+- 901
       ccaagcggatgcaccggaaacagt ggctgcggatgcGagcgtcc taggacccgaccgccca
                                                   Crawford cgcttccacgatggccacctccatggtcctcgacgcgatcgagcaagccat ctggacccg
    902 ---------+---------+---------+---------+---------+-- -------+- 961
       gcgaaggtgctaccggtggaggtaccaggagctgcgctagctcgttcggta GACCTGGGC
                                                              SEQ ID: 2 ccaacaagaagg cgtactcgacctgaaagacgttatccaccatacggataggggatctca    3'
    962 ---------+--- ------+---------+---------+---------+---------+- 1021
           GGTTGTTCTTCC gcatgagctggactttctgcaataggtggtatgcctatccctagagt     5'
```

FIGURE 4

```
                                                                    SEQ ID: 1
5'      ggaccacgatcgctgatccggccacagcccgtcccgccgatctcgtccagcgccgc TTCG
    721 ---------+---------+---------+---------+---------+------ ---+ 780
3'      cctggtgctagcgactaggccggtgtcgggcagggcggctagagcaggtcgcggcg aagc GACCACCAGCACCTAACC ggctgtgggtagcagacctcacctatgtgtcgacctgggcag
    781 ---------+-------- -+---------+---------+---------+---------+ 840
        ctggtggtcgtggattgg ccgacacccatcgtctggagtggatacacagctggacccgtc B         BamHI
        ggttcgcctacgtggcctttgtcaccgacgcct acgCtcgcaggatcctgggctggcgggt
    841 ---------+---------+---------+--- ------+---------+---------+- 901
        ccaagcggatgcaccggaaacagtggctgcgga tgcGagcgtcctaggacccgaccgccca B'                                  C   D
        cg cttccacgatggccacctccatggtcctcg acgcgatcgagcaagccatctggacccg
    902 -- ------+---------+---------+--- ------+---------+---------+- 961
        gc gaaggtgctaccggtggaggtaccaggagc tgcgctagctcgttcggtaGACCTGGGC
                                                              SEQ ID: 2
        C'   D'
        ccaacaagaagg cgtactcgacctgaaagacgttatccaccatacggataggggatctca   3'
    962 --------+--- ------+---------+---------+---------+---------+- 1021
        GGTTGTTCTTCC gcatgagctggactttctgcaataggtggtatgcctatcccctagagt   5'
```

IS6110 BASED MOLECULAR DETECTION OF MYCOBACTERIUM TUBERCULOSIS

FIELD OF INVENTION

The inventions described and claimed herein relate to the design and composition of an assay to determine infection due to *Mycobacterium tuberculosis* by detecting the *M. tuberculosis* insertion element IS6110 in any clinical specimen. The inventions described and claimed herein also relate to the design and composition of a "Universal" method of extracting nucleic acids from all types of clinical specimens. The inventions described and claimed herein also relate to the design and composition of two nucleic acid primers capable of specifically amplifying a portion of IS6110 in a polymerase chain reaction, and a restriction endonuclease and electrophoresis based test for identifying the amplified IS6110 DNA.

BACKGROUND OF THE INVENTION

*Mycobacterium tuberculosis* is expected to kill 3 million people in 1995 (Dolin et al.), making tuberculosis the world's number one cause of death due to an infectious agent. The number of new people getting infected each year is on the rise and is currently estimated at 8.8 million. An increase in HIV infection, and changing global migration and travel patterns have led to a resurgence of this disease in the industrialized nations.

Tuberculosis is caused by infection due to *M. tuberculosis*, with a few cases being caused by *M. bovis*. Several dozen species of Mycobacteria are known, and most are non-pathogenic for humans. Early tuberculosis often goes unrecognized in an otherwise healthy individual. Classical initial methods of diagnosis include examination of a sputum smear under a microscope for acid-fast mycobacteria and an x-ray of the lungs. However, in a vast majority of cases the sputum smear examination is negative for Mycobacteria in the early stages of the disease, and lung changes may not be obvious on an x-ray until several months following infection. Another complicating factor is that acid-fast bacteria in a sputum smear may often be other species of mycobacteria.

Antibiotics used for treating tuberculosis have considerable side effects, and must be taken as a combination of three or more drugs for a six to twelve month period. In addition, the possibility of inducing the appearance of drug resistant tuberculosis prevents therapy from being administered without solid evidence to support the diagnosis. Currently the only absolutely reliable method of diagnosis is based on culturing *M. tuberculosis* from the clinical specimen and identifying it morphologically and biochemically. This usually takes anywhere from three to six weeks, during which time a patient may become seriously ill and infect other individuals. Therefore, a rapid test capable of reliably detecting the presence of *M. tuberculosis* is vital for the early detection and treatment.

Several molecular tests have been developed recently for the rapid detection and identification of *M. tuberculosis*. A commercial test, the Gen-Probe "Amplified *Mycobacterium tuberculosis* Direct Test" has been evaluated by Abe et al and Miller et al. This test amplifies *M. tuberculosis* 16S ribosomal RNA from respiratory specimens and uses a chemiluminescent probe to detect the amplified product with a reported sensitivity of about 91%. Other commercial tests based on ligase chain reaction (LCR) (Abbott Laboratories), polymerase chain reaction (PCR) (Roche Diagnostics Systems, Eastman Kodak Co., Johnson & Johnson), Q-beta replicase (Gene Trak), and strand displacement amplification (Becton Dickinson) are discussed in a review by Forbes.

The development of polymerase chain reaction (PCR) (Saiki et al.), which allows DNA to be amplified and detected from small amounts of nucleic acid samples has made it possible to detect *M. tuberculosis* specific nucleic acids in clinical specimens. Some of the earlier reports were based on the detection of the 16S ribosomal RNA or it's gene. The discovery of the IS6110 insertion element (Cave et al., Eisenach et al., Thierry et al.) and the belief that this element may only be present in *M. tuberculosis* complex (*M. tuberculosis, M. bovis, M bovis-BCG, M. africanum* and *M. microti*) spawned a whole series of rapid diagnostic strategies (Brisson-Noel et al., Clarridge et al., Cormican et al., Cousins et al., Del Portillo et al., Folgueira et al., Forbes et al., Hermans et al., Kaltwasser et al., Kocagoz et al., Kolk et al., Kox et al., Liu et al., Miller et al., Pao et al., Reischl et al., Schluger et al., Shawar et al., Wilson et al., Zambardi et al.). These tests employ various techniques to extract DNA from the sputum. PCR is used to amplify IS6110 DNA sequences from the extracted DNA. The successful amplification of this DNA is considered to be an indicator of the presence of *M. tuberculosis* infection. U.S. Pat. Nos. 5,168,039 and 5,370,998 have been issued to Crawford et al. for the IS6110 based detection of tuberculosis. European patent EP 0,461,045 has been issued to Guesdon for the IS6110 based detection of tuberculosis. The IS6110 element is present at ten, two, one, five and five copies in *M. tuberculosis, M. bovis, M. bovis-BCG, M. africanum* and *M microti* respectively (Spargo et al.).

Most reports using IS6110 based detection of tuberculosis claim sensitivities of over 75% and specificities approaching 100%. However, a blind comparison study among 7 major laboratories authored by Noordhoek et al. raised a major concern when it reported false positive rates of 3 to 77% and sensitivities ranging from 2 to 90%. This study was significant because it allowed all participating laboratories to use their own detection strategies to identify IS6110, and the final results clearly indicate that existing protocols are severely deficient in terms of both sensitivity and specificity. Another study by Lee et al. reported false positives of 62% while analyzing cerebrospinal fluid samples obtained from patients with tubercular meningitis. While specimen contamination from amplified IS6110 DNA originating from previously processed samples in the same laboratory may explain some false positives, this is not a major source of error because most laboratories maintain excellent specimen containment procedures to avoid contamination. Another possibility exists, and this is the occurrence of IS6110 like sequences in organisms other than *M. tuberculosis*. IS6110 is a transposable insertion element (Calos and Miller), and these fragments of DNA have the property of being "mobile". Insertion elements in DNA can under certain situations "jump" from their original location in the genome of an organism and move to another site in the same genomic DNA. There is also evolutionary data to show that insertion elements have often moved and evolved between organisms. This fact is well known to those versed in the field of molecular biology. IS6110 is also likely to have originated from (or been passed on to) other organisms, and certain regions of DNA may have remained conserved among these organisms during evolution. This raised the possibility that some laboratories may have amplified stretches of DNA related to IS6110 from organisms that were not *M. tuberculosis*. This would explain some of the false positive tests reported in the literature. In order to address this issue, we carried out a systematic analysis of nucleic acid sequences deposited in GenBank and found stretches of sequences similar to IS6110 in organisms other than *M. tuberculosis*. Many of these organisms are found in clinical specimens. A report published by Mariani et al. also discusses the horizontal transfer between organisms of sequences related to the *M. tuberculosis* IS6110 element. Additionally, Kent et al. were able to amplify sequences related to IS6110 from Mycobacteria other than *M. tuberculosis*, confirming the suspicion that IS6110 like sequences were present in other organisms, and that they could be detected in a PCR carried out with putatively IS6110 specific primers designed to detect *M. tuberculosis*.

The design of the PCR amplification primers has to be carefully selected and optimized for specificity for IS6110. Primers designed without consideration to their priming specificity may hybridize to IS6110 related sequences from other organisms and may yield what appear to be correctly sized amplified DNA. Subsequent analysis of this amplified DNA by assays based on hybridization, if carried out under less that ideal conditions can lead to a false positive test. Fidler et al. also state that some primers based on IS6110 sequence may or may not be specific for the IS6110 gene.

Another drawback of the published protocols is that most methods used for extracting nucleic acids cannot easily be used on specimens other than sputum. Any nucleic acid extraction that necessitates a tedious and inefficient DNA purification will decrease the speed and sensitivity of the test. Additionally, having to carry out a different extraction procedure on non-sputum samples also makes the whole process expensive and slow. Operator safety is also a major concern when handling samples containing live *M. tuberculosis*, and many published protocols for nucleic acid purification are incapable of removing all live organisms.

It was clear from published reports that no existing technique based on IS6110 provided a level of confidence needed in a clinical diagnostic test. We carried out a systematic analysis of the various parameters involved in nucleic acid extraction and have developed and optimized a protocol that is safe, efficient and can be used without modification to purify nucleic acids from any organism present in any type of clinical specimen. We then analyzed the known IS6110 like sequences available from GenBank and developed nucleic acid primers capable of amplifying only IS6110 and no other known nucleic acid sequence from related genes.

Specimen contamination by preexisting amplified DNA in laboratories is a major concern in diagnostic laboratories as it leads to false positive results. Our amplified DNA identification strategy is rapid and is also designed to inactivate the amplified DNA by cleaving it into two parts. This renders the DNA unamplifiable in a subsequent PCR amplification.

In this disclosure, we systematically analyzed and developed a "Universal" specimen preparation protocol, developed IS6110 specific PCR primers, and an amplified DNA identification and inactivation strategy to provide a complete "specimen to result" protocol.

SUMMARY OF THE INVENTION

The detection of IS6110 DNA in a clinical specimen is a rapid way of diagnosing infection by *Mycobacterium tuberculosis*. A reliable diagnostic test for tuberculosis based on the IS6110 insertion element is described in this disclosure. A "Universal" specimen preparation protocol that eliminates live organisms and purifies nucleic acids from all types of clinical specimens is described. Two nucleic acid primers designed to amplify IS6110 DNA with high specificity in a polymerase chain reaction are also described. The amplified IS6110 DNA is identified by a combined restriction endonuclease and electrophoresis assay. The identification process also renders the DNA unamplifiable in a subsequent PCR, thereby reducing the possibility of contaminating other specimens. Time, labor and cost are minimized, while user safety and test reliability are maximized. The complete DNA extraction, amplification and analysis is accomplished within an 8 hour period, with a sensitivity of 92% and a specificity approaching 100%. Testing of serially obtained samples from the same patient increases the overall rate of detection to 100%.

BRIEF DESCRIPTION OF THE DRAWINGS

FIG. 3 shows the locations of the PCR primers (underlined) and the SalI (GTCGAC) restriction enzyme site described in the Crawford et al. patents. The locations of our primers SEQ ID NO: 1 and SEQ ID NO: 2 are shown in upper case, along with the restriction enzyme site BamHI (GGATCC) used in our detection technique.

FIG. 4 shows the locations of three PCR primers (underlined) B, C and D described in the Guesdon et al. patent. The locations of our primers SEQ ID NO: 1 and SEQ ID NO:2 are shown in upper case, along with the restriction enzyme site BamHI (GGATCC) used in our detection technique.

DETAILS OF THE INVENTION

Figure 1:
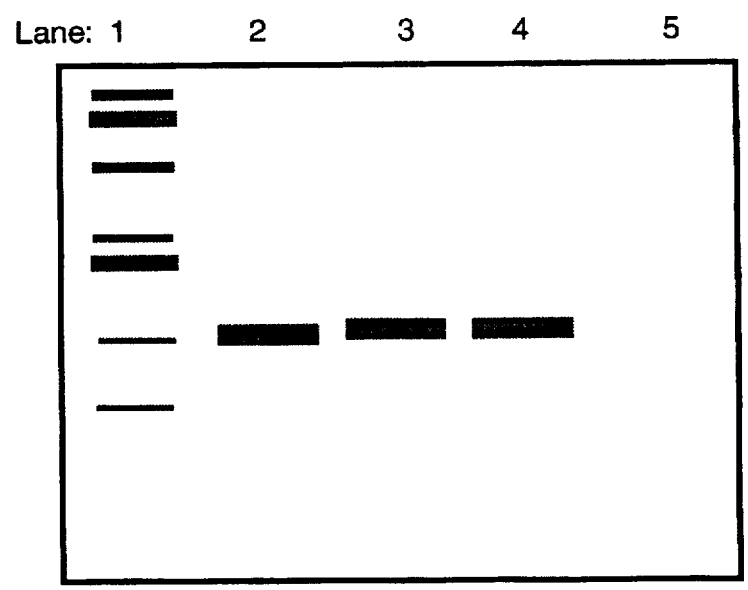
FIG. 1 is an example of correct and incorrect priming, with PCR carried out on isolates of *M. smegmatis* and *M. tuberculosis* using primers for IS6110 (GGTGCGTAAG TGGGTGCGCC AGGC and GCAGATCGAC TCGACAC-CCC AC).

The objective of this work has been to develop a comprehensive combination of techniques that allow for reliable, rapid and safe detection of *M. tuberculosis*. The limiting steps in any PCR based diagnostic scheme are sample lysis, DNA extraction, specific DNA amplification and amplified DNA (amplicon) identification.

Purification of nucleic acids from clinical specimens, which may vary in age from minutes to samples archived for years, is a difficult task. Liquid specimens range in consistency from watery like urine and cerebrospinal fluid, to thicker substances like pus, congealed blood or sputum. Solid specimens can vary from organ biopsies to slides made from tissue sections. There is no commonly accepted "standard" protocol for the preparation of samples for determination of the presence of *M. tuberculosis*. The magnitude of this problem is made obvious by the fact that publications describing the PCR based diagnosis of TB describe a multitude of different DNA extraction techniques. Common methods use one or more of the following reagents to lyse cells and extract nucleic acids. The specimen is lysed by mixing in reagents containing enzymes, detergents, alkalis, organic solvents or chaotropic agents. After varying periods of exposure, a variety of techniques are used to separate the nucleic acids from these lytic reagents. We compared the results of lysing *M. tuberculosis* in enzymes, detergents, alkalis and organic solvents and discovered that simply boiling cell suspensions of cultured *M. tuberculosis* in plain water for 15 minutes was better than using any lytic reagent. In a series of experiments, serial dilutions of a *M. tuberculosis* culture were subjected to lysis by treatment with lytic reagents consisting of either enzyme, detergent, alkali or organic solvent, followed by boiling in a water bath for 15 minutes. PCR was carried out on these lysates. Surprisingly, control tubes containing only *M. tuberculosis* resuspended in water showed a detection sensitivity 10 fold greater than tests using any lytic reagent. We found that we could amplify DNA from an equivalent of 2 colony forming units of *M. tuberculosis*. The safety of boiling lysis was evaluated and it was determined that a suspension of *M. tuberculosis* culture inside a 1.5 ml polypropylene screw cap tube, when placed in a boiling water bath became non-viable in 15 minutes. Therefore 15 minutes in boiling water was sufficient to completely kill all live *M. tuberculosis* and render the specimen safe for further analysis. This finding is similar to the results reported by Zwadyk Jr. et al.

While it is easy to boil a pure culture of *M. tuberculosis*, it is inadvisable to boil a clinical specimen because the proteins in the specimen tend to coagulate, and as a consequence all DNA released by the lysed cells gets trapped in this coagulum, making it impossible to further purify the nucleic acids. Further experiments showed that the addition of guanidine thiocyanate prevented proteins from coagulating and allowed us to boil clinical specimens. We further discovered that the addition of alkaline phenol (pH 8.0) to the guanidine thiocyanate would allow us to preferentially purify DNA from the lysed specimen. The presence of guanidine thiocyanate and phenol makes this reagent combination extremely lytic and sterilizing. When followed by chloroform extraction and centrifugation in the same tube, DNA preferentially separates into the aqueous phase from which it is easily precipitated by exposure to alcohol. We have used this quick and simple universal lysis and DNA extraction procedure to process over 1000 specimens ranging from pure cultures of mycobacteria and fungi, to sputum, broncho-alveolar lavage fluid, tissue homogenates, cerebrospinal fluid, urine, blood, wound swabs and scrapings from paraffin embedded slides of tissues. Universal lysis provides high quality DNA from virtually any organism that may be present in body fluids and tissues, thus eliminating the need for carrying out specialized "organism or specimen specific" forms of lysis. The only technique simpler than the universal lysis procedure is boiling a sample in water. While boiling in water frequently works for pure cultures, the addition of a chaotrope like guanidine thiocyanate is required to prevent proteinaceous material in clinical specimens from coagulating and irretrievably trapping the DNA. The presence of chemicals that inhibit PCR amplification is also a major concern, and our "Universal" lysis appears to avoid this pitfall. This may be related in part to our use of guanidine thiocyanate, since Brisson-Noel et al. report that this chemical removes PCR inhibitors from otherwise unamplifiable specimens.

Our DNA extraction procedure resembles a technique described by Chomczynski and Sacchi where they utilized acid guanidinium thiocyanate-phenol-chloroform to preferentially extract RNA from cells and tissues. Our method differs from their technique in several ways. Their cell lysis is carried out at room temperature (22° C.), in order to maintain the integrity of the RNA. We carry out cell lysis by boiling at 100° C. The boiling serves several important functions. It lyses the cell walls of hard to lyse pathogens like fungi and mycobacteria. Boiling in the presence of guanidine thiocyanate dissolves insoluble tissue fragments and coagulated proteinaceous debris that would otherwise trap DNA. The boiling kills infectious agents and makes the specimens safe for handling by laboratory personnel. Finally the boiling breaks up chromosomes into smaller fragments of DNA which are less likely to be trapped in cellular debris and therefore easier to purify. Chomczynski and Sacchi used acid guanidinium thiocyanate-phenol-chloroform to extract RNA from cells and tissues, while we use alkaline guanidine thiocyanate-phenol-tris to preferentially extract DNA from a diverse variety of clinical specimens. An alkaline phenol environment serves a vital purpose, because under alkaline conditions the RNA preferentially remains in the organic phase and is discarded, while the DNA safely separates out into the aqueous phase from which it is recovered by isopropanol precipitation. Acidic conditions described by Chomczynski and Sacchi may irreversibly damage the DNA by depurinating and breaking the DNA into small unamplifiable fragments, and the acid environment also causes the DNA to preferentially separate into the organic phase and be discarded during the preferential separation of RNA into the aqueous phase. At least three companies market kits containing a guanidine-phenol reagent for extracting RNA (RNAzol by Tel-Test, Friendswood, Tex. and TRIzol by Life Technologies, Gaithersburg, Md.) or RNA/DNA/Protein (Tri Reagent by Molecular Research Center, Cincinnati, Ohio). All use room temperature extractions and can be used on cell cultures and homogenized tissues. We are aware of no report describing the use of boiling lysis in alkaline guanidine thiocyanate-phenol-tris to extract DNA from pathogenic organisms in clinical specimens. Neither the Chomczynski and Sacchi technique, nor any of the protocols used by these commercial kits describes their utility for clinical specimens. In their present forms, all four methods are incapable of providing PCR quality DNA from all clinical specimens with the ease and efficiency of our protocol. In addition, pathogens like fungi and mycobacteria will not be lysed completely by these reagents at room temperature, and pose a potential health hazard to laboratory personnel.

Our "Universal" DNA extraction protocol is used as described. 200 ul of a liquid specimen like sputum, broncho-alveolar lavage fluid, cerebrospinal fluid, urine, or other body fluids/exudates is used. For thick purulent samples 100 ul of specimen is mixed with 100 ul of sterile water. Dilute specimens like urine may be concentrated by centrifugation. 100 ul of blood is mixed with 100 ul of sterile water. Clots (if any) are broken up by pipetting up and down several times. 50 ul of bacterial, fungal, viral or mycobacterial cultures is diluted with 150 ul of sterile water. For plate cultures, a loopful of organisms is resuspended in 200 ul of sterile water by vortexing. Swabs from infected sources are dipped in a microcentrifuge tube containing 300 ul of sterile water and squeezed out against the sides of the tube. 200 ul is used for sample preparation. Solid tissues are homogenized in sterile water, while sections mounted on slides are scraped off the slide using a sterile scalpel and resuspended in 200 ul of sterile water. The objective of all methods described in this paragraph is to break up any clinical specimen as finely as possible and to resuspend it in a volume of 200 ul of aqueous liquid. Virtually any clinical specimen can be processed by one of these methods.

1.5 ml Sarsted (Newton, N.C.) polypropylene screw cap tubes with o-ring seals were used for the extractions. 200 ul of specimen was added to 500 ul of alkaline guanidine thiocyanate/phenol/tris (GPT) reagent (6M guanidine thiocyanate dissolved in 50 mM tris pH 8.3, mixed with an equal volume of phenol buffered in tris pH 8.0). This was mixed by vortexing and immediately placed in a boiling water bath for 15 minutes. The tubes were spun in a microcentrifuge for 5 seconds. 250 ul of chloroform/isoamyl alcohol (24:1 by volume) was added and mixed by vortexing. The liquid phases were separated by centrifugation in a microcentrifuge at 14,000 rpm for 10 minutes, and 450 ul of aqueous (upper) phase was transferred to a fresh tube. The aqueous phase was mixed with 500 ul of 100% isopropanol and placed at −20° C. for at least 1 hour (it may be left at −20° C. overnight). At the end of this period the tubes were centrifuged in a microcentrifuge at 14,000 rpm for 15 minutes and the supernatant was removed without disturbing the nucleic acid pellet. The pellet was washed with 500 ul of ice-cold 70% ethanol to remove traces of GPT reagent by gently inverting 2 times and then centrifuged for 5 minutes. The ethanol was removed and the pellet dried in a speed vac for 10 minutes. The DNA pellet was resuspended in 25 ul of deionized water and 5 ul (1 ul in the case of pure culture lysates) was used in a 50 ul PCR amplification.

The development of the "Universal" specimen lysis and DNA extraction protocol completed our first objective of rapidly, safely and reliably purifying DNA from virtually any given clinical specimen. Our "Universal" lysis protocol is also described in our U.S. patent application (Ser. No. 08/373,127, filed January 1995) titled "Nucleic acid probes for the detection and identification of fungi". European Patent EP 0 556 521 A1, "Sample processing using disinfectant" (Dey et al., December 1992) describes a variety of chemicals for use in extracting DNA from mycobacteria. None of the methods described relate to our "Universal" lysis and DNA extraction strategy.

Our next goal was to develop a set of PCR primers that would be used to amplify DNA from the IS6110 insertion element with high specificity and sensitivity. Our main purpose was to try and avoid the pitfalls faced by other laboratories which caused them to experience a large number of false positive specimens as discussed in the background section (Noordhoek et al., Lee et al. Kent et al.). As a first step towards specificity, we analyzed the sequences in GenBank to identify sequences from other organisms that had any identity to the *M. tuberculosis* IS6110 sequence. 1360 bp of IS6110 sequence obtained from GenBank was edited into 200 bp sections and each 200 bp unit was used to search GenBank for related sequences. The purpose was to identify sub-regions of the IS6110 DNA that share common sequence motifs with genes from other organisms. Some sequences with areas of identity large enough to provide false priming sites for PCR primers include *Mycobacterium smegmatis* insertion sequence IS1137, *Pseudomonas syringae* insertion sequence IS51, *Pseudomonas cepacia* insertion sequence IS401, *Escherichia coli* transposon Tn3411 and *Agrobacterium tumefaciens* Ti plasmid (GenBank accession numbers X70913, M14365, L09108, M19532, X55075). While some of these organisms are never found in clinical specimens, the existence of these sequences strongly supports the possibility of encountering more related sequences (as yet undiscovered) in organisms capable of colonizing the respiratory tract.

FIG. 1 is an appropriate demonstration of how a primer pair used to amplify IS6110 from *M. tuberculosis* can easily amplify a non-IS6110 DNA from a different organism. Since both the correct amplicon as well as the incorrect amplicon look exactly the same on a gel, it would be easy to mistake the non-IS6110 amplicon as being IS6110, resulting in a false positive test for tuberculosis. The photograph in FIG. 1 shows the gel containing the DNA amplified during a PCR carried out on *M. smegmatis* and two isolates of *M. tuberculosis* using IS6110 primers having the sequences GGT-GCGTAAG TGGGTGCGCC AGGC and GCAGATCGAC TCGACACCCC AC. The *M. smegmatis* IS1137 insertion element, which only differs by a few bases at these priming sites, generates an amplicon of approximately the same size as that expected for an IS6110 amplicon. Lane 1 shows phi X-174 HaeIII size marker, lane 2 shows *M. smegmatis*, lanes 3 & 4 show two isolates of *M. tuberculosis*, lane 5 shows negative control for PCR amplification.

Designing a highly specific nucleic acid primer for use in a PCR amplification requires careful consideration of all factors associated with successful primer design. One of the most important aspects is the location, composition and priming specificity of the last few bases present at the 3' end of a primer. As long as the 3' bases anneal perfectly to a stretch of DNA, the primer is available for amplification in a PCR, and unintended target sequences may get amplified as demonstrated in the preceding paragraph. It is therefore essential that the 3' ends of both primers for a PCR amplification be highly specific for the desired target sequence. The importance of the priming specificity of the 3' end of a PCR primer has also been demonstrated by Sommer et al. while diagnosing mutations and polymorphisms in human genes.

Once regions of IS6110 common to other genes were identified, these were excluded as potential sites for PCR primers. An intensive comparative analysis of the IS6110 element and related sequences was carried out. Sites for PCR primers that would be specific for IS6110 and would be sensitive enough to work in the presence of DNA from several organisms (most clinical specimens have human, bacterial, viral and fungal DNA mixed together in various proportions) were not obvious and to the best of our knowledge had not been reported in the literature. After analyzing hybridization characteristics, secondary structure and thermal profiles, several potential primers were selected in regions that were "unique" to IS6110. Potential primers were then compared to all genes in GenBank and all primers having significant identity with regions in other genes were eliminated. The few remaining potential primer pairs were reassessed for base composition, thermal stability, annealing characteristics, unique 3' ends, absence of hairpins, GC content and absence of primer dimer formation. Two primers that met most of criteria were selected: Primer SEQ ID NO: 1=TTCGGACCAC CAGCACCTAA CC and primer SEQ ID NO: 2=CCTTCTTGTT GGCGGGTCCA G.

Any DNA extracted from respiratory tract specimens will contain human DNA along with DNA from bacteria inhabiting this region. Therefore, we tested our primers for ability to amplify human DNA as well as DNA isolated from a variety of bacteria and mycobacteria. Pooled sputum obtained from individuals with no history of tuberculosis was also tested to determine primer specificity. This pooled sputum was expected to contain a representative sampling of most bacteria, fungi and viruses likely to be present in the human respiratory tract. Any DNA capable of yielding a false positive test should potentially be detected in the pooled sputum. Also tested were several mycobacteria that do not cause tuberculosis, but may appear in sputum smears as acid fast organisms. PCR was carried out in an attempt to identify any related sequences that may be amplifiable with our primer pair (SEQ ID NO: 1 and SEQ ID NO: 2). The PCR reagents were made and dispensed in a clean room dedicated to PCR reagent preparation. No specimen, culture or purified DNA was ever introduced into the PCR mix room. Target DNA was added to the PCR mix in a separate room which has never been exposed to amplified DNA. Amplification was carried out in a Perkin-Elmer 9600 thermal cycler (Norwalk, Conn.) using Perkin-Elmer 200 ul thin walled tubes with attached individual caps. The first solution added to the PCR tube contained 2.5 ul of 10× PCR buffer (100 mM tris pH 8.3, 500 mM KCl, 15 mM $MgCl_2$), 5.0 ul of 50% glycerol/1 mM cresol red, 8.0 ul of dNTP mix (1.25 mM each of dATP, dGTP, dTTP and dCTP), 2.0 ul of primer SEQ ID NO: 1=TTCGGACCAC CAGCACCTAA CC (5 picomoles/ul), 2.0 ul of primer SEQ ID NO: 2=CCTTCTTGTT GGCGGGTCCA G (5 picomoles/ul) and 5.5 ul of water. One Ampliwax PCR Gem-50 wax bead (Perkin-Elmer, Norwalk, Conn.) was added and the tubes placed in a heating block at 80° C. for 30 seconds and cooled to room temperature to form a barrier of wax. 20 ul of a solution containing 2.5 ul of 10× PCR buffer, 5.0 ul of 50% glycerol/1 mM cresol red, 12.3 ul of water and 0.2 ul Taq polymerase (AmpliTaq 5 U/ul, Perkin-Elmer) was added to each tube. The tubes were removed from the mix preparation room and 5.0 ul DNA template from the "Universal lysis" was added to each tube. The tubes were placed for 1 minute in a thermal cycler preheated to 94° C. and then subjected to 50 cycles of amplification at 94° C. for 30 sec., 65° C. for 30 sec. and 72° C. for 1 min., followed by final extension at 72° C. for 10 min.

Following the PCR, 10 ul of each sample was run on a 5% polyacrylamide mini-gel in 1× TBE (0.1M tris, 0.09M boric acid, 1 mM EDTA, pH 8.3) buffer at 200 volts for 20 min. The gel was stained with 0.5 ug/ml of ethidium bromide in 1× TBE for 4 min. and visualized on a short-wave UV transilluminator. As shown in Table 1, only DNA from *M. tuberculosis* and *M. bovis* yielded an appropriately sized amplicon. This finding indicated that our primers were specific for IS6110, and would not give false positives with a non-IS6110 target. It should be noted that no false positive was observed with *M. smegmatis*, even though it contains an insertion element closely resembling the IS6110 element. Additionally, no false positives were seen with DNA from *M. avium*, *M. intracellulare*, *M. fortuitum*, *M. kansasii*, *M. xenopi*, *M. malmoense* or *M. chelonae*, unlike the finding of Kent et al. where they demonstrate the ability to amplify IS6110 like sequences from these organisms using primers designed to amplify *M. tuberculosis* IS6110 DNA.

TABLE 1

Specific amplification of IS6110 from *M. tuberculosis* and *M. bovis* using primers SEQ ID NO:1 and SEQ ID NO:2

| Specimen | PCR | Specimen | PCR |
| --- | --- | --- | --- |
| Homo sapiens DNA | − | *M. chelonae* | − |
| Pooled "normal" sputum | − | *M. fortuitum* | − |
| Acinetobacter sp. | − | *M. gordonae* | − |
| Actinomyces sp. | − | *M. intracellulare* | − |
| Aspergillus fumigatus | − | *M. kansasii* | − |
| Corynebacteria sp. | − | *M. malmoense* | − |
| Cryptococcus laurentii | − | *M. marinum* | − |
| Escherichia coli | − | *M. nonchromogenicum* | − |
| Nocardia asteroides | − | *M. phlei* | − |
| Peptostreptococcus sp. | − | *M. scrofulaceum* | − |
| Proprionibacterium sp. | − | *M. simiae* | − |
| Rhodococcus sp. | − | *M. smegmatis* | − |
| Streptococcus sp. | − | *M. szulgai* | − |
| Streptomyces sp. | − | *M. triviale* | − |
| *M. avium* | − | *M. tuberculosis* | + |
| *M. bovis* | + | *M. xenopi* | − |

The presence of a correctly sized amplicon on a gel is not sufficient to establish the identity of the amplicon. Amplicon identification is most accurately done by directly sequencing the DNA and comparing it with the known sequence for IS6110. At present this is not a cost effective measure and takes about 24 hours to accomplish. Analysis of the amplified DNA using one of the various formats based on probe hybridization, as discussed in U.S. Pat. No. 4,851,330 issued to Kohne, is an effective analytical tool, but it may take up to one day to process a set of samples. Additionally, excessive handling of amplified DNA poses an additional contamination problem, as amplified DNA may end up contaminating specimens being tested for IS6110 and will be reamplified, resulting in a false positive test. It is therefore important to observe PCR contamination prevention strategies.

Our next goal was to develop an amplicon identification method that would be reliable, and that would inactivate the amplified DNA and prevent it from being amplified any further by our PCR primers SEQ ID NO: 1 and SEQ ID NO: 2. Restriction enzymes are highly specialized proteins which recognize specific sequences on double stranded DNA. Restriction enzymes bind to these specific sites on DNA and hydrolyze a phosphodiester bond on each strand of DNA, producing a "cut". The fragment of IS6110 amplified by our primers SEQ ID NO: 1 and SEQ ID NO: 2 has a stretch of 6 base DNA sequence that reads GGATCC. This sequence is located approximately 110 bases from one end of the amplicon and approximately 85 bases from the other end. The GGATCC sequence is the recognition and cleavage site for the restriction endonuclease enzyme, BamHI or an isoschizomer. An isoschizomer for BamHI would be any different restriction enzyme that cuts DNA at the same sequence as BamHI. When the IS6110 amplicon generated by SEQ ID NO: 1 and SEQ ID NO: 2 is incubated with the enzyme BamHI, the amplicon is cleaved into two pieces, 110 and 85 base pairs in length. These two DNA fragments are detected by gel electrophoresis, and confirm the identity of the amplified DNA. Cutting the amplified DNA into two parts also disrupts the linear integrity of the DNA and prevents it from acting as a template for further amplification in a PCR carried out with primers SEQ ID NO: 1 and SEQ ID NO: 2. This in effect sterilizes the amplified DNA and decreases the possibility of a full length amplicon contaminating other specimens.

Amplicon size, combined with appropriate restriction site analysis, is an accurate and very rapid analytical tool. A series of 40 or so samples can be analyzed within 1.5 hours. The use of restriction fragments to identify sections of DNA are well known to those versed in this art.

Upon completion of the PCR, the amplified DNA remains sealed below a layer of solidified wax. The restriction endonuclease digestion is carried out by placing 25 ul of a mix containing 7.5 ul of 10× BamHI buffer, 16.5 ul of water and 1 ul (10 U) of BamHI restriction endonuclease (Boehringer Mannheim, Indianapolis, Ind.) on top of this wax. The wax barrier is broken with a pipette tip and the two liquids mixed by gentle pipetting. The tubes are placed at 37° C. for 20 minutes to complete the digestion of any amplified IS6110 DNA. An aliquot of each sample is electrophoresed on a 5% polyacrylamide mini-gel in 1× TBE (0.1M tris, 0.09M boric acid, 1 mM EDTA, pH 8.3) buffer at 200 volts for 20 min. The gel was stained with 0.5 ug/ml of ethidium bromide in 1× TBE for 4 minutes. Any DNA present is visualized on a short-wave UV transilluminator. The presence of two bands, 110 and 85 bp in size, confirms the presence of IS6110.

Figure 2:
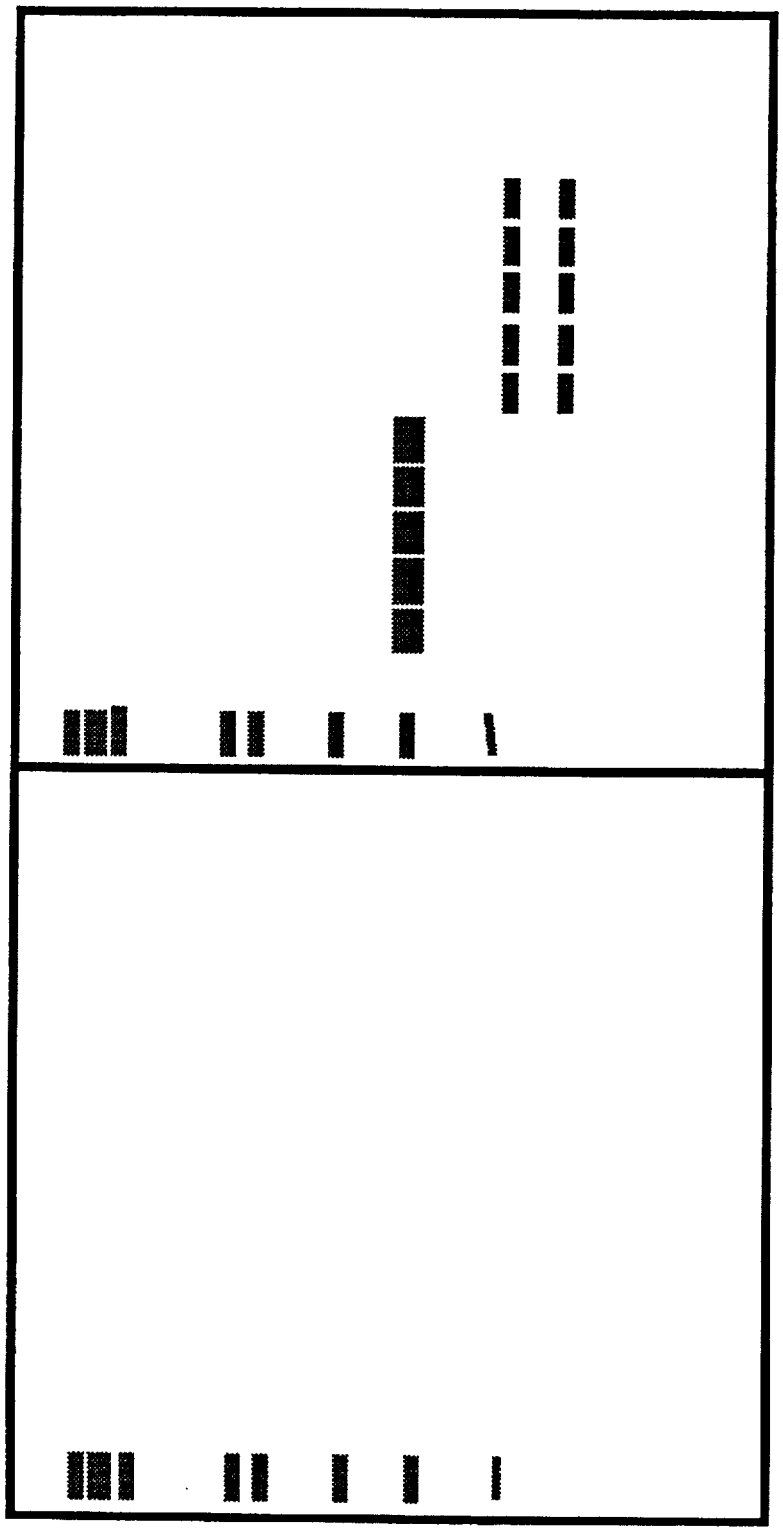
FIG. 2 shows amplification and restriction endonuclease digestion of IS6110.

FIG. 2 shows the results of a PCR amplification carried out on a panel of mycobacteria using primers SEQ ID NO: 1 and SEQ ID NO: 2. Only *M. bovis* and 4 different isolates of *M. tuberculosis* yielded an amplicon. A BamHI restriction endonuclease digest of all 5 amplicons shows an identical pattern of two DNA fragments and confirms the presence of IS6110. FIG. 2 is a photograph of two adjacent 5% polyacrylamide gels containing 15 lanes each. (Lanes 1 & 16: phi X-HaeIII size marker. Lanes 2 to 15: *M. malmoense, M.*

*intracellulare, M. fortuitum, M. gordonae, M. smegmatis, M. phlei, M. nonchromogenicum, M. xenopi, M. szulgai, M. kansasii, M. triviale, M. marinum, M. simiae, M. chelonae.* Lane 17: *M. avium.* Lane 18: *M. bovis.* Lanes 19 to 22: four isolates of *M. tuberculosis.* Lanes 23 to 27: BamHI digests of *M. bovis* and four *M. tuberculosis* amplicons from lanes 18 to 22. Lanes 28 to 30: negative controls for PCR amplification.)

The sensitivity of PCR procedures is directly influenced by the efficacy of the lytic procedure and by the amplification conditions. As noted earlier, the presence of alkali, detergent, organic solvent or protease reduced the sensitivity by about 10-fold as compared to boiling the sample in plain water. Secondly, we found that a hot-start PCR amplification using a wax barrier in the manner described by us increased the sensitivity of our test by at least 1000-fold as compared to a traditional cold-start PCR amplification. This was done by comparing serially diluted *M. tuberculosis* DNA under hot-start and cold-start amplification conditions. In a cold start reaction, all reagents are mixed in a PCR tube at room temperature. This low temperature allows some primers to anneal to each other and to non-specific DNA targets, and Taq polymerase adds dNTPs to extend these incorrectly annealed primers. This loss of primers decreases the amount of reagents left to amplify the desired target gene. In a hot-start reaction, the primers and dNTPs are kept segregated from the Taq polymerase and DNA template by a wax barrier. This barrier is melted when the tubes are placed in the thermocycler and heated to 94° C. Even with hot-start, an occasional sample (usually less than 1% of the total number of specimens tested) will form a primer dimer that can be seen on polyacrylamide gel electrophoresis. The presence of a primer dimer indicates a potential failure of the PCR due to a reduction in sensitivity, and a repeat of the analysis is indicated. This improvement in amplification by prevention of primer dimer formation was originally noted by Chou et al.

The individual components of all protocols described in the details of the invention were combined into one comprehensive protocol designed to make the detection of tuberculosis extremely rapid, reliable and cost effective. This diagnostic protocol can be completed within an 8 hour period, thus providing a diagnosis on the same day. An efficient "Universal" specimen preparation protocol that eliminates live organisms and purifies nucleic acids from all types of clinical specimens, combined with two nucleic acid primers designed to amplify IS6110 DNA with high specificity in a polymerase chain reaction gives our protocol high reliability. The identification process also renders the DNA unamplifiable in a subsequent PCR, thereby reducing the possibility of contaminating other specimens.

This speed, safety, sensitivity and specificity, combined with the ease of use and low cost has to the best of our knowledge not been addressed by any report. We have systematically analyzed and optimized all significant variables required to develop a reliable PCR based test for tuberculosis. The importance, contribution to the test results, and the integration of the variables addressed by us are not obvious and have never before been addressed in a comprehensive manner with an aim of optimizing all stages of sample handling and testing in order to provide a complete test procedure. In U.S. Pat. No. 5,168,039, Crawford et al. describe the use of the IS6110 gene, and it's subclones, as hybridization probes for the detection of tuberculosis. We have avoided the use of time consuming hybridization based detection and instead rely upon restriction endonuclease digestion with BamHI to rapidly identify the amplified DNA. This also decreases the possibility of a false hybridization of a probe to an incorrectly amplified sequence related to IS6110. An additional U.S. Pat. No. 5,370,998 issued to Crawford et al., describes 2 PCR primers that amplify a 123 bp fragment of IS6110 containing a SalI restriction enzyme site. A process for extracting DNA from one type of specimen (sputum) is also described. The entire process of detecting IS6110 in a sputum specimen is reportedly accomplished in 48 hours. Our detection strategy can be used on all clinical specimens (as opposed to only sputum specimens described by Crawford et al.), and our entire detection process can be completed within 8 hours.

European patent EP 0 461 045 A1 has been issued to Guesdon for the IS6110 gene based detection of tuberculosis. They describe 8 PCR primers (A, B, C, D, E, F, G, H) to be used in various combinations (A with B, C or D, and H with G) to amplify IS6110. A DNA extraction strategy is not described, and a claim is made that oligonucleotide primers having 80% identity to those described will also successfully detect IS6110. While this may be true on a pure culture of *M. tuberculosis,* the premise is self defeating because primers not having a high level of specificity can potentially amplify unrelated genes.

FIG. 3 shows the locations of the PCR primers (underlined) and the SalI (GTCGAC) restriction enzyme site described in the Crawford et al. patents. The locations of our primers SEQ ID NO: 1 and SEQ ID NO: 2 are shown in upper case, along with the restriction enzyme site BamHI (GGATCC) used in our detection technique. Primer SEQ ID NO: 1 overlaps one Crawford et al. primer by 5 bases and has a 3' end located 17 bases away from the 3' end of the Crawford et al. primer. It should be noted that our primers SEQ ID NO: 1 and SEQ ID NO: 2 have unique 3' ends not related to the Crawford et al. primers, and that this unique priming specificity enables us to detect IS6110 with a high level of confidence. In the *Mycobacterium tuberculosis* IS6110 sequence, the number of the first base is as shown in the GenBank sequences, accession numbers X17348 and M29899. The Crawford et al. primer sequence described in the patent has a single additional base that is missing from the GenBank sequences. This base has been added to the sequence shown here and is marked with a bold, upper case 'C' in the primer sequence.

FIG. 4 shows the locations of three PCR primers (underlined) B, C and D described in the Guesdon et al. patent. The locations of our primers SEQ ID NO: 1 and SEQ ID NO:2 are shown in upper case, along with the restriction enzyme site BamHI (GGATCC) used in our detection technique. Primer SEQ ID NO: 2 overlaps the Guesdon et al. primer C and D by 11 and 16 bases respectively, and has a 3' end located 19 and 16 bases away from the ends of the Guesdon et al. primers. It should be noted that our primers SEQ ID NO: 1 and SEQ ID NO: 2 have unique 3' ends not related to any of the Guesdon et al. primers. In the *Mycobacterium tuberculosis* IS6110 sequence, the number of the first base is as shown in the GenBank sequences, accession numbers X17348 and M29899. The Guesdon et al. primer sequences B, C and D are shown underlined, with BB', CC' and DD' marking the two ends of each primer sequence. Primer B described in the patent has a single additional base that is mising from the GenBank sequences. This base has been added to the sequence shown here and is marked with a bold, upper case 'C' in the primer sequence.

Further variations of the invention will be apparent to those with ordinary skill in the art. The following exemplifies various aspects of the invention but is not intended to limit its usefulness.

EXAMPLE 1

Specific Amplification and Restriction Endonuclease Based Identification of TB in Clinical Specimens Combined tuberculosis detection protocol comprising Universal lysis, specific IS6110 amplification, restriction endonuclease amplicon analysis and amplicon sterilization tested on clinical specimens.

We tested 104 sputum specimens by culture and found that 48 were positive for *M. tuberculosis*, while an additional 24 tested positive for other mycobacterial species. These sputum specimens were then subjected to our complete IS6110 based tuberculosis detection strategy. This consisted of Universal lysis and DNA extraction on each sputum specimen, hot-start PCR amplification using primers SEQ ID NO: 1 and SBQ ID NO: 2. BamHI restriction endonuclease digestion and sterilization of amplicon and polyacrylamide mini-gel electrophoresis. The results are shown in Table 2. Our technique detected 44 out of 48 specimens that were positive for *M. tuberculosis* on culture. Our results showed a sensitivity of 92% (44 out of 48) for the identification of sputum containing culturable *M. tuberculosis*. However, in clinical testing more than one sputum sample (taken serially over a period of days) is analyzed by culture. In a similar manner, serially obtained samples from the 4 "false negative" patients were also tested for IS6110. In each case, all other samples from these 4 patients tested positive for IS6110. Therefore, the realistic rate of detection of this test approaches 100% if more than one specimen is tested from each patient.

TABLE 2

|  | PCR positive | PCR negative |
| --- | --- | --- |
| Culture positive (*M. tuberculosis*) | 44 | 4 |
| Culture positive (other mycobacteria) | 0 | 24 |
| Culture negative (previous TB) | 25 | 3 |
| Culture negative | 1 | 3 |

In addition, our test detected 25 out of 28 specimens that came from patients who had previously tested positive on culture for *M. tuberculosis* and had received complete treatment for tuberculosis. No *M. tuberculosis* was cultured at the present time from the sputum of these 28 patients. The treatment for tuberculosis kills *M. tuberculosis* and renders it unable to propagate in culture. However, remnants of these non-viable organisms continue to persist and are shed in the sputum for many years following therapy. These can be detected using PCR amplification based tests which do not depend on the presence of live mycobacteria, and can actually identify traces of DNA fragments left behind from a previous tuberculosis infection. This observation is known to people versed in this art.

All specimens containing other mycobacterial species tested negative for IS6110. One specimen from a patient with no history of tuberculosis tested positive for IS6110 by PCR. Sputum from this patient was smear positive for acid fast bacilli, indicating the presence of some species of mycobacterium, but yielded no growth on culture. Potentially, this patient had a subclinical infection that ultimately resolved itself with the persistence of a substantial load of non-viable organisms.

The presence of amplification inhibitors is a concern while analyzing clinical specimens and many laboratories routinely add internal amplification controls to each sample tested. We have not observed a carry over of inhibitors with universal lysis, and false negatives appear to be a function of sampling limitations rather than a carry over of inhibitors. Each PCR amplification reaction only tests a very small volume of sputum, while the volume of sputum utilized for culture based identification is much greater. The addition of internal positive controls, while being scientifically sound, can and does decrease the sensitivity of amplification by consuming amplification reagents that would otherwise be used in the identification of the real IS6110 target. Any addition of internal positive control, that may mask the presence of 1 or 2 copies of IS6110 is unacceptable.

As shown in this example, complete DNA extraction, amplification and analysis is accomplished with ease within an 8 hour period, with a sensitivity of 92% and a specificity approaching 100%. Testing of serially obtained samples from the same patient increases the overall rate of detection to 100%.

EXAMPLE 2

DNA Sequence Based Identification of Tuberculosis

Another utility of our primers SEQ ID NO: 1 and SEQ ID NO: 2 is in the sequence based identification of *M. tuberculosis*. These primers are used to amplify IS6110 DNA from any clinical specimen, and the amplified DNA is sequenced using either primer SEQ ID NO: 1 or primer SEQ ID NO: 2. If the resulting sequence or its complement matches SEQ ID NO: 3, the identity of the amplicon will be confirmed as the *M. tuberculosis* IS6110 insertion element. The sequence may be generated using any of the current methods of DNA sequence determination or any future developments or modifications of this technology.

EXAMPLE 3

Capillary Electrophoresis Based Identification of Amplified IS6110 DNA

Primers SEQ ID NO: 1 and SEQ ID NO: 2 may be labeled with any fluorescent moiety, and used in a PCR to amplify IS6110 DNA from any clinical specimen. Following amplification the fluorescently labeled amplified DNA is subjected to restriction digestion using restriction endonuclease BamHI. The fragments of DNA generated are then subjected to separation and size analysis by capillary electrophoresis and the presence of two fragments 110 and 85 bp in length confirms the identity of IS6110 DNA.

EXAMPLE 4

Capture and Identification of IS6110 DNA

Both primers described in this disclosure may be labeled with any detectable moiety including, but not limited to radioisotopes, enzymes, antigens, antibodies, chemiluminescent reagents and fluorescent chemicals. Primers SEQ ID NO: 1 and SEQ ID NO: 2 may also be modified without changing the substance of their purpose by terminal addition of nucleotides designed to incorporate restriction sites or other useful sequences. Additional modifications designed to assist in the solid phase capture and/or purification of these IS6110 sequences, or any sequences hybridized to SEQ ID NO: 1, SEQ ID NO: 2, SEQ ID NO: 3 or their complements, include, but are not limited to moieties like para-magnetic particles, biotin, fluorescein, digoxigenin, antigens and antibodies.

Some utilities of these modifications include, but are not limited to the following. Primer SEQ ID NO: 1 or SEQ ID NO: 2 is labelled with biotin or any moiety designed to assist in the solid phase capture, for example using streptavidin coated para-magnetic particles or other solid phase. Following amplification of target IS6110 DNA from a clinical specimen, the solid phase is used to capture DNA and this is subsequently hybridized to a third probe labeled with a detectable moiety. This third probe may be a subset of SEQ ID NO: 3 designed to overlap and detect the BamHI restriction sequence.

As an alternative, SEQ ID NO: 1 and SEQ ID NO: 2 are labeled with a detectable signal moiety and used in a PCR, following which a third probe (SEQ ID NO: 3 or a subset thereof) attached to a solid phase is used to capture the amplified, labeled DNA for analysis.

Another option would be to capture DNA amplified with SEQ ID NO: 1 and SEQ ID NO: 2 by hybridization to a subset of SEQ ID NO: 3 which is bound to a solid phase like a DNA hybridization "chip" and another subset of SEQ ID NO: 3 labeled with a detection moiety is used to detect the presence of the bound DNA.

IS6110 sequences amplified by SEQ ID NO: 1 and SEQ ID NO: 2 may also be identified by ligating 2 oligonucleotides across the BamHI restriction site. One of these two oligonucleotides may be labeled with a capture and the other with a detection moiety. The ability to detect the detection moiety following solid phase capture of the capture moiety would confirm successful ligation of the two oligonucleotides. These two additional oligonucleotides would be a subset of SEQ ID NO: 3.

Additionally, all identification strategies described herein may also be carried out without PCR amplification if adequate signal is generated by the detection moiety. This may be accomplished by attaching multiple detectable moieties in a probe sequence. Branched DNA probes are appropriate for the addition of a large number of detectable moieties, making direct detection feasable.

We recognize that present and future technologies could be adapted to use RNA or modified synthetic sequences functionally equivalent to DNA sequences (SEQ ID NO: 1), (SEQ ID NO: 2), and (SEQ ID NO: 3), as described in this application. Other variations in this technology will be apparent to those with skill in the art.

---

We claim:

1. A process for the detection of the presence of *Mycobacterium tuberculosis* or *Mycobacterium bovis* in a sample, comprising the step of:
   detecting the presence of a DNA segment consisting of (SEQ ID NO:3) or its complement in the sample, indicating the presence of *Mycobacterium tuberculosis* or *Mycobacterium bovis* in the sample; wherein said DNA segment is not detected in the sample absent the presence of either *Mycobacterium tuberculosis* or *Mycobacterium bovis*.

2. The process of claim 1 which additionally comprises the step of amplifying (SEQ ID NO:3) or its complement, prior to detecting the presence of said DNA segment.

3. The process of claim 2 wherein polymerase chain reaction is used to amplify (SEQ ID NO:3) or its complement, and the primers used in the polymerase chain reaction are (SEQ ID NO:1) and (SEQ ID NO:2) or their complements.

4. The process of claim 1 in which said sample is sputum, broncho-alveolar lavage fluid, cerebrospinal fluid, urine or other body fluid, exudate, or tissue.

5. A process for the detection of the presence of *Mycobacterium tuberculosis* or *Mycobacterium bovis* in a sample, comprising the steps of:
   a. lysing the cells in said sample by boiling in the presence of guanidine thiocyanate, organic solvent and alkaline buffer,
   b. isolating the genomic DNA contained in said cells, and
   c. analyzing said DNA to determine the presence of (SEQ ID NO:3) or its complement, indicating the presence of *Mycobacterium tuberculosis* or *Mycobacterium bovis* in the sample; wherein the presence of (SEQ ID NO:3) or its complement is not detected in the sample absent the presence of either *Mycobacterium tuberculosis* or *Mycobacterium bovis*.

6. The process of claim 5 which additionally comprises the step of amplifying a portion of said isolated DNA before determining the presence of (SEQ ID NO:3) or its complement.

7. The process of claim 6 wherein polymerase chain reaction is used to amplify (SEQ ID NO:3) or its complement, and the primers used in the polymerase chain reaction are (SEQ ID NO:1) and (SEQ ID NO:2) or their complements.

8. The process of claim 7 which additionally comprises the step of inactivating the amplified DNA by adding a restriction endonuclease enzyme after the amplification reaction.

9. The process of claim 8 in which said enzyme is BamHI or an isoschizomer recognizing the same nucleic acid sequence.

10. The process of claim 5 in which said organic solvent is phenol, and said alkaline buffer is tris buffer.

11. A process for the detection of the presence of *Mycobacterium tuberculosis* or *Mycobacterium bovis* in a sample, comprising the steps of:
   a. lysing the cells in said sample by boiling in the presence of alkaline guanidine thiocyanate,
   b. isolating the genomic DNA contained in said cells,
   c. amplifying said isolated DNA, and
   d. analyzing the products of the amplification to determine the presence of (SEQ ID NO:3) or its complement, indicating the presence of *Mycobacterium tuberculosis* or *Mycobacterium bovis* in said sample; wherein the presence of (SEQ ID NO:3) or its complement is not detected in said sample absent the presence of either *Mycobacterium tuberculosis* or *Mycobacterium bovis*.

12. The process of claim 11 wherein polymerase chain reaction is used to amplify said isolated DNA, and the primers used in the polymerase chain reaction are (SEQ ID NO:1) and (SEQ ID NO:2) or their complements.

13. A process for the detection of the presence of *Mycobacterium tuberculosis* or *Mycobacterium bovis* in a sample, comprising the steps of:
   a. lysing the cells in said sample by boiling in the presence of an aqueous alkaline guanidine thiocyanate solution for 15 minutes,
   b. isolating the genomic DNA contained in said cells by centrifugation and precipitation,
   c. amplifying said isolated DNA using polymerase chain reaction in which the primers used in the polymerase chain reaction are (SEQ ID NO:1) and (SEQ ID NO:2) or their complements, and
   d. analyzing the products of the amplification to determine the presence of (SEQ ID NO:3) or its complement, indicating the presence of *Mycobacterium tuberculosis* or *Mycobacterium bovis* in the sample; wherein the presence of (SEQ ID NO:3) or its complement is not detected in the sample absent the presence of either *Mycobacterium tuberculosis* or *Mycobacterium bovis*.

14. A DNA sequence consisting of (SEQ ID NO:3) or its complement for determination of the presence of *Mycobacterium tuberculosis* or *Mycobacterium bovis* in a sample.

15. The process of claim 5 wherein said DNA is analyzed by rapid mini-gel electrophoresis.

16. The process of claim 1 wherein said segment is RNA or a synthetic sequence modified for incorporation of a restriction site or for solid phase capture wherein said synthetic sequence is SEQ ID NO: 3 or its complement.

17. The process of claim 3 wherein the primers are RNA or synthetic sequences modified for incorporation of a restriction site or for solid phase capture wherein said synthetic sequences are SEQ ID NO: 1 and 2 or their complements.

18. The process of claim 3, wherein said primers are labelled with a detectable moiety.

19. The process of claim 18, wherein said detectable moiety is selected from the group consisting of radioisotopes, enzymes, antigens, antibodies, chemiluminescent reagents and fluorescent chemicals.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: nucleic acid probe for M. tuberculosis
        IS6110 gene ( i i i ) HYPOTHETICAL: NO ( i v ) ANTI-SENSE: NO ( v ) SEQUENCE DESCRIPTION: SEQ ID NO: 1:

TTCGGACCAC CAGCACCTAA CC      2 2

( 2 ) INFORMATION FOR SEQ ID NO:2:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: nucleic acid probe for M. tuberculosis
        IS6110 gene ( i i i ) HYPOTHETICAL: NO ( i v ) ANTI-SENSE: NO ( v ) SEQUENCE DESCRIPTION: SEQ ID NO: 2:

CCTTCTTGTT GGCGGGTCCA G      2 1

( 2 ) INFORMATION FOR SEQ ID NO:3:

( i ) SEQUENCE CHARACTERISTICS:

(A) LENGTH: 197
(B) TYPE: nucleic acid
(C) STRANDEDNESS: single
(D) TOPOLOGY: linear (i i) MOLECULE TYPE: DNA segment of IS6110 gene from
Mycobacterium tuberculosis complex, base number
777 to base 973

(i i i) HYPOTHETICAL: NO (i v) ANTI-SENSE: NO (v) SEQUENCE DESCRIPTION: SEQ ID NO: 3:

| TTCGGACCAC | CAGCACCTAA | CCGGCTGTGG | GTAGCAGACC | TCACCTATGT | 50 |
| GTCGACCTGG | GCAGGGTTCG | CCTACGTGGC | CTTTGTCACC | GACGCCTACG | 100 |
| CTCGCAGGAT | CCTGGGCTGG | CGGGTCGCTT | CCACGATGGC | CACCTCCATG | 150 |
| GTCCTCGACG | CGATCGAGCA | AGCCATCTGG | ACCCGCCAAC | AAGAAGG    | 197 |